(12) United States Patent
Zhang et al.

(10) Patent No.: US 8,936,780 B2
(45) Date of Patent: Jan. 20, 2015

(54) STIMULI RESPONSIVE POLYESTER AMIDE PARTICLES

(75) Inventors: Gina Zhang, Temecula, CA (US); Jessica Renee DesNoyer, San Jose, CA (US); Gordon Stewart, San Francisco, CA (US); Maricela Kezis, San Diego, CA (US); Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2449 days.

(21) Appl. No.: 11/468,721

(22) Filed: Aug. 30, 2006

(65) Prior Publication Data

US 2008/0057024 A1    Mar. 6, 2008

(51) Int. Cl.
  *A61K 31/785*  (2006.01)
  *A61F 2/00*  (2006.01)
  *A61K 9/00*  (2006.01)
  *A61L 24/00*  (2006.01)
  *A61L 24/04*  (2006.01)

(52) U.S. Cl.
  CPC ............. *A61K 9/0019* (2013.01); *A61L 24/001* (2013.01); *A61L 24/046* (2013.01); *A61L 2430/36* (2013.01); *Y10S 977/906* (2013.01)
  USPC ......... 424/78.27; 424/423; 977/906; 525/437

(58) Field of Classification Search
  None
  See application file for complete search history.

(56) References Cited

U.S. PATENT DOCUMENTS

| | | | |
|---|---|---|---|
| 5,759,563 A * | 6/1998 | Yewey et al. | 424/426 |
| 5,919,893 A * | 7/1999 | Roby et al. | 528/310 |
| 6,692,466 B1 | 2/2004 | Chow et al. | |
| 6,703,040 B2 * | 3/2004 | Katsarava et al. | 424/444 |
| 7,273,469 B1 | 9/2007 | Chan et al. | |
| 2004/0009229 A1 | 1/2004 | Unger et al. | |
| 2004/0170685 A1 * | 9/2004 | Carpenter et al. | 424/468 |
| 2005/0201972 A1 | 9/2005 | Seo et al. | |
| 2006/0034889 A1 | 2/2006 | Jo et al. | |
| 2006/0074191 A1 | 4/2006 | DesNoyer et al. | |
| 2006/0177416 A1 * | 8/2006 | Turnell et al. | 424/78.27 |

FOREIGN PATENT DOCUMENTS

| | | |
|---|---|---|
| WO | WO 2005/020933 A2 | 3/2005 |
| WO | WO-2005120453 | 12/2005 |
| WO | WO 2006/058122 A2 | 6/2006 |

OTHER PUBLICATIONS

Abbott Cardiovascular Systems, International Preliminary Report on Patentability dated Mar. 12, 2009 for PCT/US2007/018599.
PCT International Search Report and Written Opinion for PCT No. US2007/018599, mailed Apr. 23, 2008 (14 pages).
Konan-Kouakou, Y.N., et al., "In vitro and in vivo activities of verteporfin-loaded nanoparticles," Journal of Controlled Release (2005), 103:83-91.
Teixeira, M., et al., "Development and characterization of PLGA nanospheres and nanocapsules containing xanthone and 3-methoxyxanthone," European Journal of Pharmaceutics and Biopharmaceutics (2005), 59:491-500.
Win, K.Y., et al., "Effects of particle size and surface coating on cellular uptake of polymeric nanoparticles for oral delivery of anti-cancer drugs," Biomaterials (2005), 26:2713-2722.

* cited by examiner

*Primary Examiner* — Michael G Hartley
*Assistant Examiner* — Lance Rider
(74) *Attorney, Agent, or Firm* — Randy Shen; Blakely Sokoloff Taylor & Zafman LLP (57) ABSTRACT

A composition including a solution suitable for introduction into a blood vessel comprising particles including a treatment agent and a tunable stimuli-responsive polymer. A method including introducing a delivery device into a blood vessel; and introducing a solution into the blood vessel, the solution including particles comprising a treatment agent and a tunable stimuli-responsive polymer. A method including combining a treatment agent and a tunable stimuli-responsive polymer; and forming particles of the combination suitable for delivery through a blood vessel.

3 Claims, 6 Drawing Sheets

STIMULI RESPONSIVE POLYESTER AMIDE PARTICLES

BACKGROUND

1. Field

Percutaneous transluminal therapy.

2. Background

The coronary arteries supply the heart with oxygen-rich blood. When the arteries narrow, less blood and oxygen flow to the heart. The result of narrowing arteries is commonly referred to as coronary artery disease (CAD). Lack of sufficient oxygen to the heart may cause angina or a heart attack. Most cases of CAD are due to atherosclerosis (hardening of the arteries), in which fatty deposits, called plaques, build up inside the coronary arteries, restricting blood flow.

Drug therapy treats stable angina and slows coronary artery disease progression. Unstable angina may require surgical intervention in addition to the therapies given for stable angina.

To date, surgery is usually recommended for patients who have unstable angina that does not respond promptly to medical treatment, who have severe recurrent episodes that last more than 20 minutes, or who have other high risk factors for heat attacks. Surgery is also typically performed in people with severe coronary artery disease (e.g., severe angina, multi-vessel involvement, evidence of ischemia), particularly if abnormalities are evident in the left ventricle of the heart.

A number of invasive techniques are available for treating coronary artery disease. Two standard surgical procedures are coronary artery bypass grafting and percutaneous transluminal coronary angioplasty (PTCA). Studies have generally reported similar effectiveness in the two procedures, although one or the other may be preferable for specific patients. Angioplasty is less invasive than bypass and initially less expensive, although the post-operative need for medications and the high risk for repeat procedures to reopen the artery reduce the long term difference in cost. With the introduction of drug-eluting stents (DESs), the risk of repeated procedures is significantly lowered. However, bypass is still preferred for certain patient groups. For example, it is generally recommended for patients with three or more blocked arteries, or where the left main artery is narrowed by 50 percent or more, or when the diseased portion of the artery is very long. Patients with diabetes used to have a significantly better long term survival rate with bypass surgery than with angioplasty, but this difference is much offset by DES.

SUMMARY

In one embodiment, a composition is disclosed. The composition includes a solution suitable for introduction into a blood vessel including particles (e.g., microparticles or nanoparticles) including a treatment agent and a tunable, stimuli-responsive polymer. A stimuli-responsive polymer, in one aspect, is a polymer that is responsive to at least one of a physiochemical stimulus and a pharmacochemical stimulus. A physiochemical stimulus includes, but is not limited to, pH, temperature, or ionic strength. A pharmacochemical responsive polymer, is a polymer responsive to pharmacochemical stimuli, such as protein kinase upregulation, metabolites, local oxidative stress, and local free radical generation. A representative polymer is a poly(ester amide) (PEA), which is an ester amide that is biocompatible and biodegradable. The active agent includes, but is not limited to, anti-inflammatory agents and anti-proliferative agents.

In another embodiment, a method is disclosed. The method includes introducing a delivery device into a blood vessel and introducing a solution into the blood vessel. The solution, in one embodiment, includes particles, such as microparticles or nanopartices, including a treatment agent and a tunable, stimuli responsive polymer such as PEA. The delivery device may be a device such as a needle suitable for regional delivery of the solution or a percutaneously inserted transluminal catheter having a delivery port located near a treatment site.

In another embodiment, a method is disclosed that includes combining a treatment agent and a tunable, stimuli-responsive polymer and forming particles of the combination suitable for delivery through a blood vessel. Such particles may be microparticles and nanoparticles. Suitable polymers include PEAs and suitable treatment agents include anti-proliferative agents and anti-inflammatory agents.

BRIEF DESCRIPTION OF THE DRAWINGS

Features, aspects, and advantages of embodiments will become more thoroughly apparent from the following detailed description, appended claims, and accompanying drawings in which:

DETAILED DESCRIPTION

Referring to the above discussion of invasive techniques for treating coronary artery disease, to expand the minimally invasive PTCA procedure to the by-pass patient population, drug therapy may be critical based on the DES success experience. Effectively delivering anti-inflammatory and anti-proliferative drugs to disease sites therefore becomes necessary. One approach to overcome the difficulty to administer typically poorly water-soluble compounds is their incorporation in polymeric carriers (e.g., micro- or nanocarriers). Besides their ability to improve the delivery of water-soluble drugs, micro- and nanocarriers have been reported to control drug release, to reduce drug-associated adverse effects, to protect the drugs from inactivation before reaching their site of action, and to increase intracellular penetration and enhance the pharmacological activity. Normally, the polymers used for making nanoparticles are bio-degradable and bio-compatible.

In one embodiment, a composition is disclosed. The composition includes, for example, a solution suitable for introduction into a blood vessel including a treatment agent and a stimuli-responsive polymer. A stimuli-responsive polymer in one aspect is a polymer that is responsive to a physiochemical or a pharmacochemical stimuli. Representative physiochemical stimuli include, but are not limited to, pH, temperature and ionic strength. Representative pharmacochemical stimuli include, but are not limited to, protein kinase upregulation, metabolites, local oxidative stress, and local free radical generation.

In one embodiment, the active agent is an anti-inflammatory agent. Examples include, but are not limited to, mometasone, clobetasol and dexamethasone. In another embodiment, the treatment agent is an anti-proliferative agent. Examples of anti-proliferative agents include, but are not limited to, sirolimus, everolimus and paclitaxel. In another embodiment, the treatment agent may be a combination of anti-inflammatory and anti-proliferative agents. In still another embodiment, a treatment agent is an agent that would benefit a damaged blood vessel or an infarcted area. In one sense, a treatment agent is an agent that would benefit a blood vessel or an infarcted area (e.g., tissue) by itself creating new cells and/or components thereof or trigger a repair mechanism. A treatment agent may also include an agent that may benefit a blood vessel or an infarcted area (e.g., tissue) only with the assistance of another exogenous or endogenous agent. Suitable treatment agents include, but are not limited to, growth factors (e.g., vascular endothelial growth factor (VEGF), fibroblast growth factor (FGF), platelet-derived growth factor (PDGF)), cellular components, proteins, cytokines, and drugs.

In one embodiment, the stimuli-responsive polymer has an amino acid backbone. A suitable polymer with an amino acid backbone is a poly(ester amide). A poly(ester amide) (PEA) is an example of a polymer including an amino acid, a diol, and a diacid. PEA, available from MediVas, LLC of San Diego, Calif., is composed of sebacic acid, 1,6-hexanediol, leucine, lysine, acetyl end groups, and a pendant group covalently bonded to a carboxyl group of a lysine. Two forms of PEA that differ from one another in the lysine bound substituent are PEA-Benzyl and PEA-Tempo.

PEA-Benzyl is represented by the following formula:

PEA-Tempo has the general formula:

PEA-Benzyl may be made by a condensation polymerization of the three monomers (1,6-hexanediol, luecine, and lysine). PEA-Tempo is a derivative of PEA Benzyl and 4-amino-tempo. In the above formulas, "m" and "n" represent integers, each greater than one.

As noted, the PEA family of polymers includes three building blocks: an amino acid, a diol, and a diacid. A suitable PEA polymer may be modified by adding a second different amino acid. By varying the building blocks (e.g., amino acid, diol and diacid), PEA with a wide range of properties may be achieved. The tunability of these polymers is appealing as the polymer properties, such as thermal properties, mechanical properties, melting point, polymer degradation rate, polymer water uptake (e.g., hydrophobicity/hydrophilicity), can be modified to achieve a desired release rate for a treatment agent combined with the polymer. In general, PEAs with a low glass transition temperature (Tg) or that are more hydrophilic will tend to have a higher permeability for treatment agent, while PEAs with high Tgs, that are semi-crystalline, that can cross-link, or that are more hydrophobic tend to have lower permeability for treatment agent. Further, the polymer degradation rate can influence release rate of the treatment agent if the polymer begins to degrade prior to all of the treatment agent being released.

In one embodiment of PEAs, the diacid is a C2 to C 12 diacid, aliphatic (saturated) or with unsaturation. The amino acid may be glycine, valine, alanine, leucine, isoleucine or phenylalanine. An optional second amino acid may be included that could include, but is not limited to, lysine, tyrosine, glutamic acid, or cysteine. The second amino acid may contain a reactive side group that would enable the attachment (conjugation) of pharmacologically active compounds or property modifiers. For example, terminal amine and the sulfhydryl groups of, for example, lysine and cysteine side chains may be exploited to connect drugs, hormones, or other treatment agents. For liposomes and cells, conjugates can generally be prepared by modification through condensation of a protein reactive group (e.g., amine or thiol) on the phosphate group of the liposome. If a treatment agent is conjugated to the PEA backbone, a controlled (e.g., delayed) release can be obtained that will depend on the active agent linker and/or the polymer backbone.

To modify the water uptake (e.g., hydrophobicity/hydrophilicity) of a PEA, a hydrophilic diol or diamine may be conjugated to a PEA to, for example, increase the hydrophilicity which will also tend to increase its active agent permeability. Examples of hydrophilic diols or diamines include, but are not limited to, polyethylene glycol (PEG), polypropylene glycol (PPG), polyvinylpyrrolidone (PVP), hydroxyethylmethacrylate (HEMA), and hyaluronic acid.

Increasing the polyalkylene (e.g., polymethylene) chain length of the diol or diacid building block will tend to reduce the polymer Tg. PEAs based on amino acids with optical rotation (L-isomers) will tend to have a higher Tg than those based on the corresponding D, L-isomers. PEAs synthesized from L-amino acids with symmetrical side substituents (e.g., valine, leucine, phenylalanine) will tend to have higher Tgs than those synthesized from L-amino acids with nonsymmetrical side substituents (isoleucine). Amino acids with aromatic moieties (e.g., phenylalanine) will tend to have the highest Tg. Modifying the polymer in any of the ways described to increase the polymer Tg will also modify a thermal property (e.g., increase a melting point with increase of Tg) of the polymer.

Finally, the properties of a PEA or a treatment agent/PEA matrix may be modified by substituting a moiety or moieties of the basic polymer (substituting moieties of the amino acid, diol or diacid). One example is replacing the benzyl group of PEA-Benzyl with a treatment agent such as Triamcinolone acetonide (an anti-inflammatory corticosteroid).

In one embodiment, a composition including microparticles or nanoparticles of a treatment agent and a stimuli-responsive polymer (e.g., a particle described by a treatment agent partially or totally encapsulated by the polymer or conjugated to the polymer) are formed in a solution suitable for introduction into a blood vessel, such as through an injection needle or catheter. In one embodiment, the composition includes a combination of microparticles and nanoparticles. Representatively, the polymer is a PEA (e.g., PEA-Tempo, PEA-Benzyl, modified PEA) having a molecular weight of 10,000 Daltons to 20,000 Daltons (relative to polystyrene). Representatively, an average particle size of suitable microparticles or nanoparticles is on the order of ten microns or less.

In general, when PEA polymers are exposed to environments where inflammation is present (such as an active lesion, a vulnerable plaque, a border zone of infarcted tissue or a reperfused area), a PEA polymer degradation rate tends to increase with increased levels of inflammation. Consequently, by leveraging the tunability of the PEA degradation rate, a PEA-based polymer may be selected that exhibits a faster degradation rate when it encounters or is exposed to an inflammatory environment. As an extension, a degradation rate of a PEA polymer can be used to control a treatment agent release rate by, for example, conjugating the treatment agent to the polymer backbone or by ensuring that the polymer begins to degrade prior to all of the treatment agent being released from the treatment agent/polymer matrix. For example, where a treatment agent such as Triamcinolone acetonide (anti-inflammatory corticosteroid) is attached to a PEA-Benzyl by replacing the benzyl group, the treatment agent will not be released until the polymer degrades or until the link between the treatment agent and the polymer degrades.

In one embodiment, the microparticles or nanoparticles are prepared by a water/oil/water (W/O/W) double emulsion method. In the W1 phase, an aqueous phase containing treatment agent, is dispersed into the oil phase containing polymer (e.g., a PEA) dissolved in organic solvent (e.g., dichloromethane) using a high-speed homogenizer. The primary water-in-oil (W/O) emulsion is then dispersed to an aqueous solution containing a polymeric surfactant, e.g., poly(vinyl alcohol) (PVA), and further homogenized to produce a W/O/W emulsion. After stirring for several hours, the particles are collected by filtration.

In certain instances, a suitable polymer may have a glass transition temperature that is relatively low and therefore a relatively high permeability for a treatment agent. A representative glass transition temperature of such a polymer would be 36° C. to 37° C. or lower. The relatively low glass transition temperature would indicate that a treatment agent would be released relatively easily (e.g., almost immediately) upon introduction into an in vivo environment such as in a human patient. This may be desirable for certain treatment agents where, for example, it is desirable for immediate release. It may be desirable with other treatment agents, however, to slow the release rate. Alternatively, it may be desirable with the same treatment agent to create a varied or graded release rate.

One way to achieve either a slow or graded release rate with a polymer with a low glass transition temperature is to coat the particles with an additional layer or layers of the polymer. A suitable microparticle may have a coating layer in the range of one to five microns and a suitable nanoparticle may have a coating layer in the range of 50 to 80 nanometers (nm). Additional coating layers may be added to the particle by using a hydrophobic polymer in the oil phase of a water/oil emulsion. Alternatively, layers can be built up in sequence from solution by, for example, alternating layers of positively charged and negatively charged polymers, with each layer attracted to the surface by the oppositely charged layer that is already in place. For example, a polymeric form of PEA which is positively charged at many sites (through, for example, selection of positively-charged amino acids), may be used as one layer and a polymeric form of PEA which is negatively charged (through, for example, selection of negatively-charged amino acids), may be used as another layer. Other ways to control release will include selection of a surfactant in the water phase for the oil/water emulsion and tailoring the miscibility of the solvents between the oil and water phase.

The following examples illustrate degradation rates for PEA-based polymers (PEA-Benzyl and PEA-Tempo) based on levels of inflammation. The examples describe a polymer coating on a stent implant in the vasculature of pigs.

EXAMPLE 1

Figure 1:
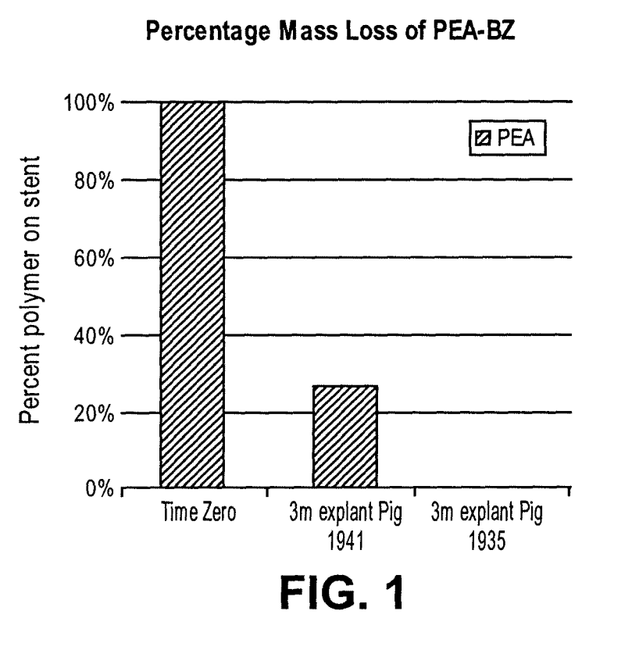
FIG. 1 shows a degradation rate of a polyester amide polymer in response to inflammation in one experimental study.

In the study, the 90-day in vivo degradation of a PEA-Benzyl sandwich construct was evaluated using the anti-proliferative agent Everolimus as a treatment agent. The Everolimus dose on the stent was 190 µg/cm². On a 3.0×13 mm PENTA™ stent (Guidant Corporation), a PEA-Benzyl primer layer was 166 µg, an Everolimus reservoir was 166 µg, and a PEA-Benzyl topcoat was 575 µg. FIG. 1 shows the percentage mass loss of PEA-Benzyl between zero and 90 days. Referring to FIG. 1, Pig 1941 is representative of the degradation rate when there are low levels of inflammation, while pig 1935 exemplifies the changes that occur in the degradation rate when there are high levels of inflammation.

FIG. 1 shows the degradation rate of PEA-Benzyl varied, depending on the pig, and more specifically, on the inflammation levels within the animal in which the stents were implanted. In Pig 1941, the animal with low levels of inflammation, 24 percent of the polymer remained on the stent at 90 days, while in Pig 1935, the animal with high levels of inflammation, no polymer was detectable on any of the stents after 90 days. Within the same pig, the sample variation was small.

EXAMPLE 2

In the study, the 90-day in vivo degradation rate of a PEA-Tempo matrix plus topcoat construct was studied using Everolimus as the treatment agent. The Everolimus dose was 190 µg/cm². On a 3.0×13 mm PENTA™ stent, the PEA-Tempo/Everolimus reservoir layer was 830 µg (drug (D): polymer (P)=1:4), and the PEA-Benzyl topcoat was 170 µg.

Figure 2:
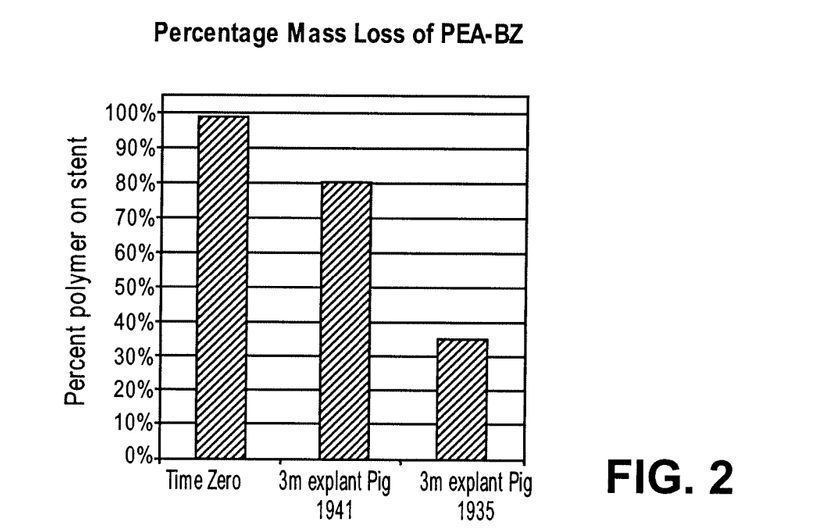
FIG. 2 shows a degradation rate of another polyester amide polymer in response to inflammation in one experimental study.
Figure 3:
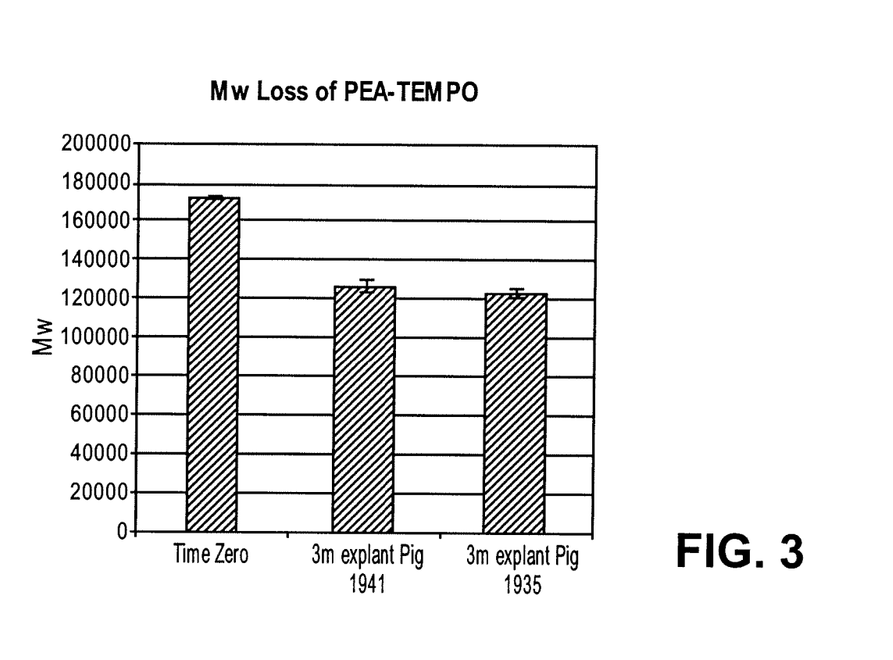
FIG. 3 shows a molecular weight change of the polymer in the experimental study described with reference to FIG. 2.

FIG. 2 illustrates the percentage mass loss of PEA-Tempo between zero and 90 days in each animal. Pig 1941 is representative of the degradation rate when there are low levels of inflammation, while Pig 1935 exemplifies the changes that occur in the degradation rate when there are high levels of inflammation. As shown by FIG. 2, the degradation rate of PEA-Tempo varied, depending on the pig, and more specifically, the inflammation levels within the animal in with the stents were implanted. In Pig 1941, the animal with low levels of inflammation, 82 percent of the polymer remained on the stent at 90 days, while in Pig 1935, the animal with high levels of inflammation, only 35 percent of the polymer remained. Within the same pig, the sample variation was small. FIG. 3 illustrates the molecular weight change of the PEA-Tempo between t0 and 90 days in each animal. Although the polymer mass loss differed greatly, depending on the levels of inflammation, the molecular weight was consistent, with about a 32 percent drop after 90 days.

EXAMPLE 3

In a second study of a PEA-Tempo construct, the in vivo degradation rate of a PEA-Tempo matrix plus topcoat construct over the course of six months was evaluated. The Everolimus dose was 100 µg/cm². On a 3.0×12 mm VISION™ stent (Guidant Corporation), the PEA-Tempo/Everolimus reservoir layer was 392 µg (D:P=1:6), and the PEA-Tempo topcoat was 400 µg. A measure of the degradation rate at the three-month time point was taken twice. For one measurement, seven stents were implanted in one pig. In the other measurement, eight stents were implanted across eight pigs. The pig in the first measurement exhibited very little inflammation, while those used in the second measurement all exhibited a great deal of inflammation.

Figure 4:
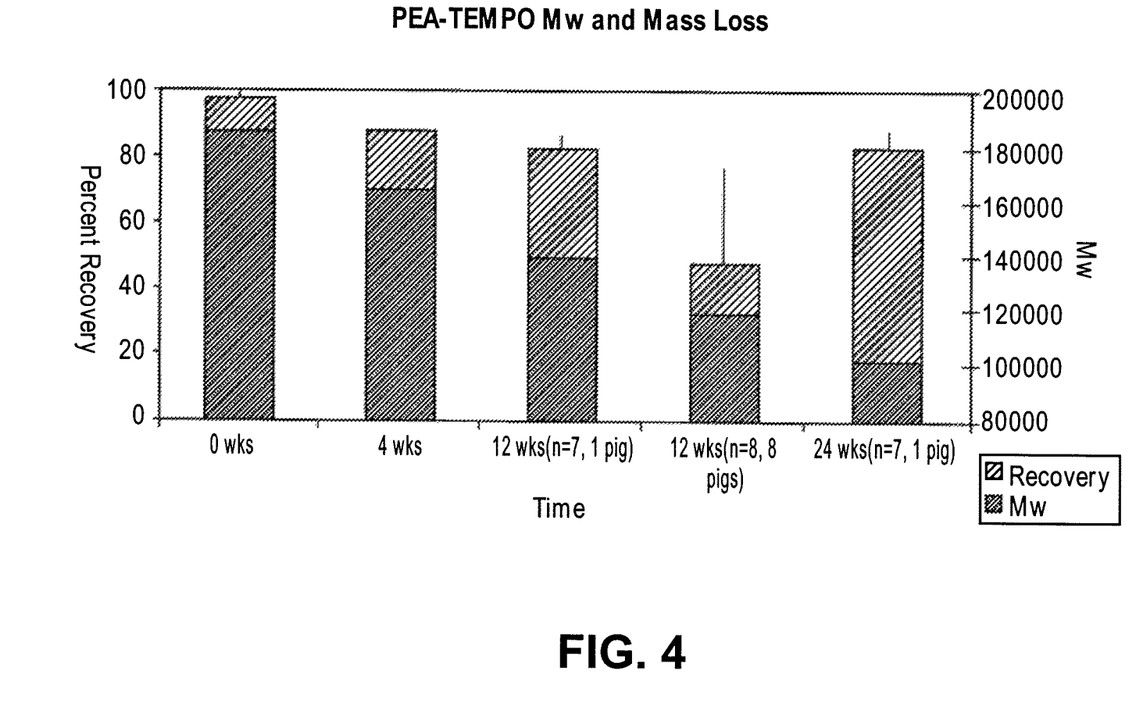
FIG. 4 shows a degradation rate and molecular weight change of another polyester amide polymer in response to inflammation in another study.

FIG. 4 illustrates both the percentage mass loss and molecular weight change of PEA-Tempo over the course of the six-month study. As shown by FIG. 4, the measured degradation rate of PEA-Tempo at three months varied. Where there was little inflammation, over 80 percent of the polymer remained on the stents, and the molecular weight dropped by only about 25 percent. These results are in line with those of Pig 1941 (low inflammation representative) in Example 2, even though the polymer was slightly different (non-acylated in Example 2) and the construct was changed. However, in the animals that exhibited high levels of inflammation, only 50 percent of the polymer remained on the stents, and the molecular weight dropped by about 36 percent. When the inflammation is kept to a minimum, the amount of polymer recovered off of the stent stays fairly constant between three and six months through the molecular weight drops, which is indicative of a bulk erosion type degradation mechanism.

In one embodiment, the composition may be delivered regionally or locally. A regional delivery may involve, for example, the injection of a composition including microparticles or nanoparticles of a treatment agent and a stimuli-responsive polymer, such as a saline solution comprising the polymers. Thus, a needle injection into a blood vessel (e.g., artery or vein), such as a radial artery or vein is suitable. In this manner, the composition may be introduced to target a treatment site within the blood vessel or beyond the blood vessel. For example, a treatment site may be a stenotic lesion within a blood vessel resulting in occlusion of a blood vessel (e.g., an occlusion of a coronary artery). Alternatively, the treatment site may be a vulnerable plaque within a blood vessel. Alternatively, a systemic delivery may target an ischemic region by, for example, traveling through the circulatory system through capillaries and arterioles associated with an ischemic region. The systemic introduction of the composition requires the composition to travel through the circulatory system to the treatment site. An advantage of PEA as the stimuli-responsive polymer is that PEA tends not to be metabolized as easily as other polymers in the liver and kidney.

Figure 5:
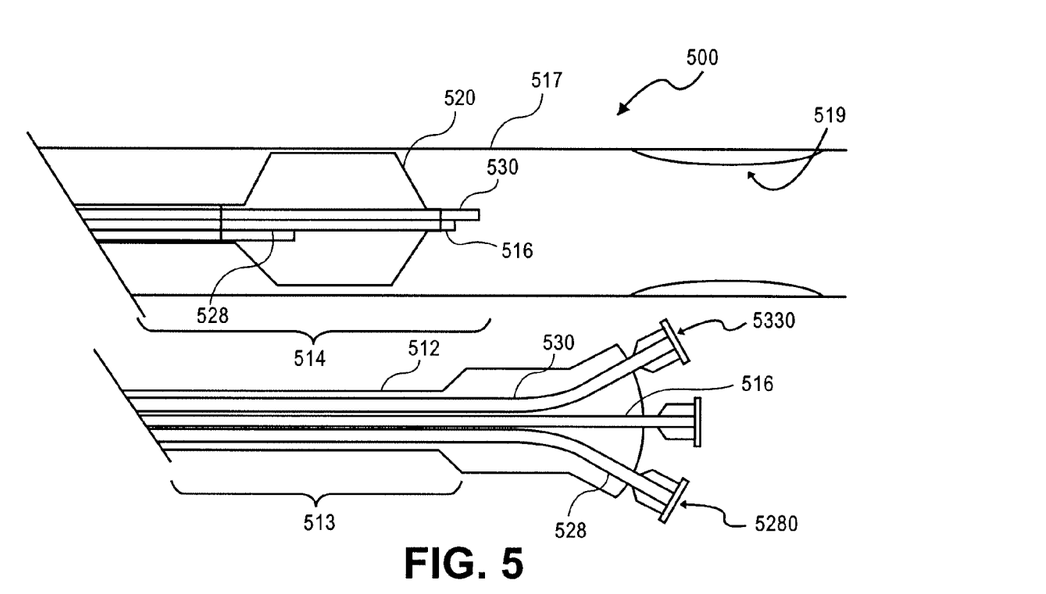
FIG. 5 shows an embodiment of a catheter assembly disposed in a blood vessel with a distal end near a treatment site within the blood vessel.

In addition to a systemic delivery, the composition may also be delivered locally. FIG. 5 illustrates one embodiment of a delivery apparatus. In general, the delivery apparatus provides a system for delivering a composition, such as stimuli-responsive polymer and an active agent to or through a desired area of a blood vessel (a physiological lumen) or tissue in order to treat a localized area of the blood vessel or to treat a localized area of tissue. The delivery apparatus described is suitable, in one embodiment, for a percutaneous delivery of an active agent where a desired form of the active agent is introduced through a single catheter lumen.

Referring to FIG. 5, the delivery apparatus includes catheter assembly 400, which is intended to broadly include any medical device designed for insertion into a blood vessel or physiological lumen to permit injection and/or withdrawal of fluids, to maintain the patency of the lumen, or for any other purpose. In one embodiment, catheter assembly 500 is defined by elongated catheter body having proximal portion 513 and distal portion 514. In one embodiment, proximal portion 513 may reside outside the patient during a procedure while distal portion 514 is placed at a treatment site, for example, within coronary blood vessel 517.

Catheter assembly 500 includes catheter body 512 having a lumen therethrough extending from proximal portion 513 to distal portion 514. In this example, guidewire cannula 516 is formed within catheter body 512 for allowing catheter assembly 500 to be fed and maneuvered over a guidewire (not shown). Guidewire cannula 516 may extend from proximal portion 513 to distal portion 514, thus describing an over the wire (OTW) assembly. In another embodiment, typically described as a rapid exchange (RX) type catheter assembly, guidewire cannula 516 extends only through a portion of catheter body 512, beginning and ending within distal portion 514. It is appreciated that a guidewire may be retracted or removed once catheter assembly 500 is placed at a region of interest, for example, within a blood vessel (e.g., artery or vein). One reason for removing a guidewire may be to utilize guidewire cannula 516 in some additional capacity such as providing a lumen for an imaging assembly or, particularly in an OTW configuration, providing a delivery lumen for a treatment agent.

In the embodiment of FIG. 5, catheter assembly 500 includes balloon 520 incorporated at distal portion 514 of catheter assembly 500 and coupled to a distal end of catheter body 512. Balloon 520 is an expandable body in fluid communication with inflation cannula 528 disposed within catheter body 512. Inflation cannula 528 extends from balloon 520 within distal portion 514 through inflation port 5280 at proximal portion 513 (e.g., at a proximal end of catheter assembly 500). Inflation cannula 528 is used to deliver a fluid to inflate balloon 520.

In the embodiment shown in FIG. 5, balloon 520 is in an expanded or inflated state that totally occludes blood vessel 517. Balloon 520 is selectively inflatable to dilate from a collapsed configuration to a desired or controlled expanded configuration. Balloon 520 can be selectively inflated by supplying a fluid (e.g., liquid) into a lumen of inflation cannula 528 at a predetermined rate of pressure through inflation port 5280. Likewise, balloon 520 is selectively deflatable to return to a collapsed configuration or deflated profile.

Balloon 520 can be made from any suitable material, including but not limited to, polymers and copolymers of polyolefins, polyamides, polyester and the like. The specific material should be compatible with an inflation or expansion fluid and must be able to tolerate the pressures that are developed within balloon 520. One suitable material is an elastomeric nylon such as PEBAX™, a condensation polymerized polyether block polyamide. PEBAX™ is a trademark of ATOCHEM Corporation of Puteaux, France.

Balloon 520 may be inflated by the introduction of a fluid (e.g., liquid) into inflation cannula 528 through inflation port 5280 at a point outside the physiological lumen). Liquids including therapeutic and/or diagnostics agents may be used to inflate balloon 520. In one embodiment, balloon 520 may be made of a material that is permeable to such therapeutic and/or diagnostic agents. In this manner, the therapeutic and/or diagnostic agent may permeate through balloon 520 into the lumen of blood vessel 517. To inflate balloon 520, suitable fluid may be supplied into inflation cannula 528 at a predetermined pressure, for example, between about one and 20 atmospheres (atm). A specific pressure depends on various factors, such as the thickness of the balloon wall, the material of which the balloon is made, the type of substance employed, and the flow rate that is desired.

Catheter assembly 500, in the embodiment shown in FIG. 5, also includes delivery cannula 530. Delivery cannula 530 extends from a proximal end of catheter assembly 500 (a proximal end of proximal portion 514) beyond a distal end of balloon 520. At a proximal portion of delivery cannula 530, located at a point outside a physiological lumen as illustrated in FIG. 5, is delivery port 5330. Delivery cannula 530 may be made of a polymer material having a lumen suitably sized to deliver a composition therethrough. In one embodiment, a composition including a treatment agent and a stimuli-responsive polymer may be introduced, in the form of a solution of microparticles or nanoparticles into delivery cannula 530 through delivery port 5330. In this manner, a composition may be delivered to a lumen of blood vessel 517. In another embodiment, a needle or hypotube may be placed in delivery cannula 530 and the composition may be introduced into a blood vessel through the needle or hypotube.

In the embodiment in FIG. 5, catheter assembly 500 is placed in blood vessel 517 so that balloon 520 and a distal end of delivery cannula 530 is proximal (upstream) from treatment site 519 that may be a lesion or vulnerable plaque. In one embodiment, balloon 520 may be inflated to occlude blood vessel 517 and therefore inhibit blood flow prior to the introduction of a composition through delivery cannula 530. In this manner, the composition is given an opportunity to interact with treatment site 519 without blood flowing through at a physiological flow rate.

In the embodiment illustrated in FIG. 5, the treatment site is a lesion or vulnerable plaque within blood vessel 519. In another embodiment, the treatment site may be capillaries or arterioles that may be associated with, for example, infarcted tissue. Thus, it may be desirable to deliver a composition including a treatment agent and a stimuli-responsive polymer to capillaries associated with or downstream of blood vessel 517. For example, a treatment agent that is a cellular component may be introduced. By interrupting a coronary blood flow with balloon 520, the dwell time of the treatment agent (cells) in the capillaries may be increased. Typically, the more time that cells are in the capillaries, the more opportunity the cells have to adhere to the capillary walls and transmigrate (travel) into the adjacent tissue where they may multiply and differentiate into tissue types that can repair infarcted tissue. It is believed that ischemic and recently infarcted (dead) tissue produce/release chemicals that signal at least some portion of the mononuclear cells in their vicinity to transmigrate toward/to their location. It is believed that the transmigrated cells differentiate and create new tissue. Similarly, other treatment agents (e.g., anti-inflammatory agents, anti-proliferative) may be introduced to target a treatment site that is ischemic tissue using the assembly of FIG. 5.

In another embodiment, an apparatus (a catheter assembly) is described for accurately locating a treatment agent at a location in a wall of a blood vessel (preferably beyond the media layer) or in a peri-adventitial space adjacent to a blood vessel, or areas radially outward from a peri-adventitial space including at tissue locations such as the tissue of the myocardium. It is appreciated that a catheter assembly is one technique for introducing treatment agents and the following description is not intended to limit the application or placement of the treatment agents described above.

Figure 6:
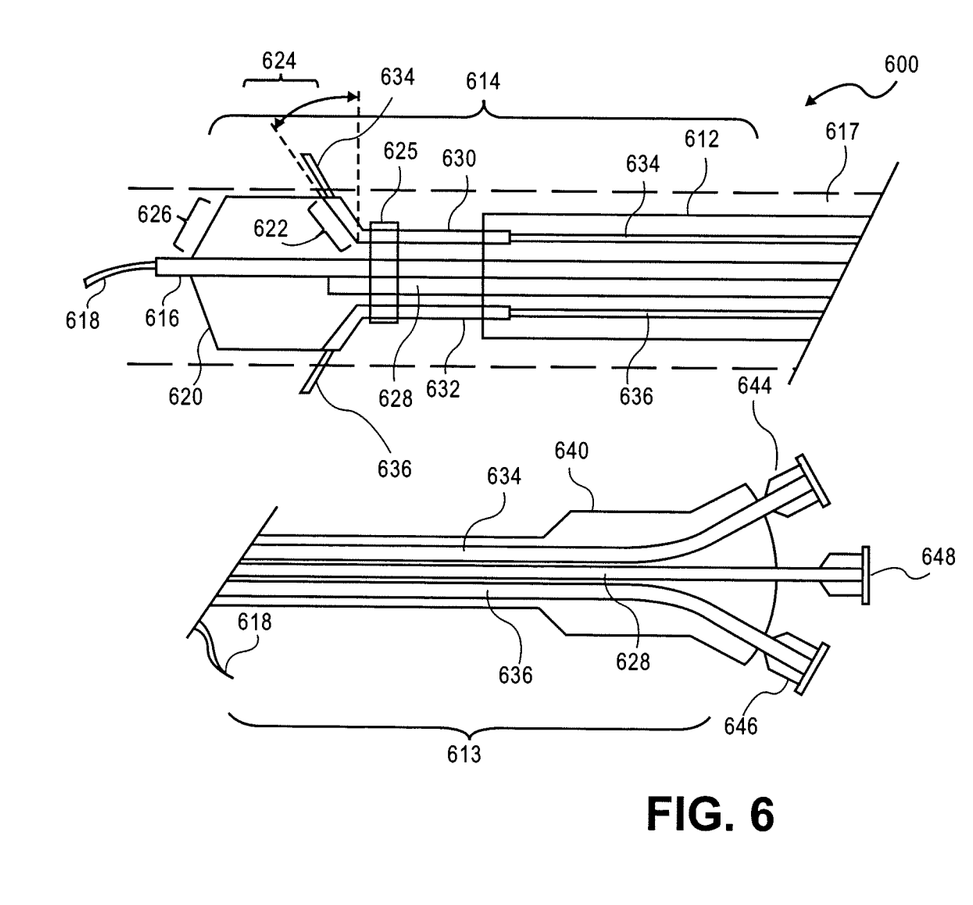
FIG. 6 shows another embodiment of a catheter assembly disposed in a blood vessel and shows a delivery device(s) extending beyond the blood vessel.

FIG. 6 illustrates one embodiment of a delivery apparatus for delivering a composition, such as a solution including micro- and/or nanoparticles of a treatment agent and a stimuli-responsive polymer, to or through a desired area of a blood vessel (a physiological lumen) or tissue in order to treat a localized area of the blood vessel or to treat a localized area of tissue possibly located adjacent to the blood vessel. The delivery apparatus is similar in certain respects to the delivery apparatus described in commonly-owned, U.S. patent application Ser. No. 09/746,498 (filed Dec. 21, 2000), titled "Local Drug Delivery Catheter with Retractable Needle," of Steward et al. (now U.S. Pat. No. 6,692,466); U.S. patent application Ser. No. 10/394,834 (filed Mar. 20, 2003), titled "Drug Delivery Catheter with Retractable Needle," of Chow et al.; and U.S. patent application Ser. No. 10/749,354 (filed Dec. 31, 2003), titled "Needle Catheter." of Chan, et al. The delivery apparatus described is suitable, in one embodiment, for a percutaneous delivery of a treatment agent/particle where a desired form of the treatment agent/particle is introduced through a single catheter needle.

Referring to FIG. 6, the delivery apparatus includes catheter assembly 600, which is intended to broadly include any medical device designed for insertion into a blood vessel or physiological lumen to permit injection or withdrawal of fluids, to maintain the patency of the lumen, or for any other purpose. In one embodiment, catheter assembly 600 is defined by elongated catheter body (cannula) 612 having proximal portion 613 and distal portion 614. In one embodiment, proximal portion 613 may reside outside a patient during a procedure while distal portion 614 is placed at a treatment site, for example, within coronary blood vessel 617.

Catheter assembly 600 includes catheter body 612 having a lumen therethrough extending from proximal portion 613 to distal portion 614. In this example, guidewire cannula 616 is formed within catheter body 612 for allowing catheter assembly 600 to be fed and maneuvered over a guidewire (guidewire 618 shown at this point within a lumen of guidewire cannula 616). Guidewire cannula 616 may extend from proximal portion 613 to distal portion 614, thus describing an over the wire (OTW) assembly. In another embodiment, typically described as a rapid exchange (RX) type catheter assembly, guidewire cannula 616 extends only through a portion of catheter body 612, for example, beginning and ending within distal portion 614. An RX type catheter assembly is shown. It is appreciated that guidewire 618 may be retracted or removed once catheter assembly 600 is placed at a region of interest, for example, within a blood vessel (e.g., artery or vein).

In the embodiment of FIG. 6, catheter assembly 600 includes balloon 620 incorporated at distal portion 614 of catheter assembly 600. Balloon 620 is an expandable body in fluid communication with inflation cannula 628 disposed within catheter body 612. Inflation cannula 628 extends from balloon 620 within distal portion 614 through inflation port 648 at proximal portion 613 (e.g., at a proximal end of catheter assembly 600). Inflation cannula 628 is used to deliver a fluid to inflate balloon 620.

In the embodiment shown in FIG. 6, balloon 620 is in an expanded or inflated state that occludes blood vessel 617. Balloon 620 is selectively inflatable to dilate from a collapsed configuration to a desired or controlled expanded configuration. Balloon 620 can be selectively inflated by supplying a fluid (e.g., liquid) into a lumen of inflation cannula 628 at a predetermined rate of pressure through inflation port 648. Likewise, balloon 620 is selectively deflatable to return to a collapsed configuration or deflated profile.

In one embodiment, balloon 620 can be defined by three portions: distal taper wall 626, medial working length 624, and proximal taper wall 622. In one embodiment, proximal taper wall 622 can taper at any suitable angle θ, typically between about 15° to less than about 90°, when balloon 620 is in an expanded (inflated) configuration.

Balloon 620 can be made from any suitable material, including, but not limited to, polymers and copolymers of polyolefins, polyamides, polyester and the like. The specific material employed should be compatible with inflation or expansion fluid and must be able to tolerate the pressures that are developed within balloon 620. One suitable material is an elastomeric nylon such as PEBAX™, a condensation polymerized polyether block polyamide. Other suitable materials for balloon 620 include, but are not limited to, a biocompatible blend of polyurethane and silicone, or a styrenic block copolymer (SBC) or blend of SBCs. Distal taper wall 626, medial working length 624, and proximal taper wall 622 can be bound together by seams or be made out of a single seamless material. A wall of balloon 620 (e.g., at any of distal taper wall 626, medial working length 624 and/or proximal taper wall 622) can have any suitable thickness so long as the thickness does not compromise properties that are critical for achieving optimum performance. Relevant properties include, but are not limited to, high burst strength, low compliance, good flexibility, high resistance to fatigue, the ability to fold, the ability to cross and recross a desired region of interest or an occluded region in a physiological lumen and low susceptibility to defects caused by handling. By way of example, not limitation, a suitable thickness of a balloon wall can be in the range of about 0.0005 inches to 0.002 inches, the specific specifications depending on the procedure for which balloon 620 is to be used and the anatomy and size of the target lumen in which balloon 620 is to be inserted.

Balloon 620 may be inflated by the introduction of a fluid (e.g., liquid) into inflation cannula 628 (through inflation port 648 at a point outside a physiological lumen). Liquids containing therapeutic and/or diagnostic agents may be used to inflate balloon 620. In one embodiment, balloon 620 may be made of a material that is permeable to such therapeutic and/or diagnostic agents. To inflate balloon 620, a suitable fluid may be supplied into inflation cannula 628 at a predetermined pressure, for example, between about one and 20 atmospheres (atm). A specific pressure depends on various factors, such as the thickness of the balloon wall, the material of which balloon 620 is made, the type of substance employed, and the flow rate that is desired.

Catheter assembly 600, in the embodiment shown in FIG. 6 also includes delivery cannula 630 and delivery cannula 632 each connected to proximal taper wall 622 of balloon 620 and extending at a proximal end, in one embodiment, into a portion of catheter body 612 of catheter assembly 600. Representatively, a suitable length for delivery cannula 630 and delivery cannula 632 is on the order of three to 6.5 centimeters (cm). Delivery cannula 630 and delivery cannula 632 can be made from any suitable material, such as polymers and copolymers of polyamides, polyolefins, polyurethanes, and the like. Catheter assembly 600, in this view, also includes needle 634 and needle 636. Needle 634 and needle 636 extend from distal portion 614 to proximal portion 613 of catheter assembly 600. At distal portion 614, needle 634 is slidably disposed through a lumen of delivery cannula 630 and needle 636 is slidably disposed through a lumen of delivery cannula 632. Thus, a dimension of delivery cannula 630 and delivery cannula 632 are each selected to be such to allow a delivery device such as a needle to be moved therethrough. Representatively, delivery cannula 630 has an inner diameter (lumen diameter) on the order of 0.002 inches to 0.020 inches (e.g., 0.0155 inches) and an outer diameter on the order of 0.006 inches to 0.05 inches (e.g., 0.0255 inches). FIG. 6 shows catheter assembly 600 with each of needle 634 and needle 636 deployed in an extended configuration, i.e., extending from an end of delivery cannula 630 and delivery cannula 632, respectively. In a retracted configuration, the needles retract proximally into the delivery cannula lumens. Representatively, delivery cannula 630 and delivery cannula 632 may be spaced radially or circumferentially from each other, for example, between 45° and 180° apart.

FIG. 6 shows delivery cannula 630 and delivery cannula 632 each connected to an exterior surface of balloon 620. Specifically, a distal end of each of delivery cannula 630 and delivery cannula 632 extend to a point equivalent to or less than a length of proximal taper wall 622 of balloon 620. One suitable technique for connecting delivery cannula 630 or delivery cannula 632 to balloon 620 is through an adhesive. A suitable adhesive includes a cyanoacrylates (e.g., LOCTITE 414™) adhesive, particularly where the balloon material is a PEBAX™ material.

Catheter assembly 600 in the embodiment shown in FIG. 6 also includes sheath ring 625. Sheath ring 625 is positioned over, in this embodiment, guidewire cannula 616, inflation cannula 628, delivery cannula 630, and delivery cannula 632, respectively. In one embodiment, sheath ring 625 functions to inhibit delamination of the delivery cannulas from proximal taper wall 622 of balloon 620 and, where thermally sealed to the various cannulas may reduce the spacing (on a proximal side of sheath ring 625) of the cannulas. Thus, a distal end of sheath ring 625 is placed, in one embodiment, at a point immediately proximal to where a delivery cannula will rotate, bend or plicate in response to the expansion or inflation of balloon 620. In one embodiment, sheath ring 625 is a biocompatible material that is capable of connecting to (e.g., bonding to) a material for balloon 620 and to a material for each of the noted cannulas that it surrounds. Representatively, a body of sheath ring 625 has a length from a proximal end to a distal end on the order of 0.25 millimeters (mm) to 0.75 mm, such as 0.5 mm.

One way to form catheter assembly 600 including sheath ring 625 is to initially connect (e.g., bond) balloon 620 at a distal end to guidewire cannula 616. Balloon 620 is also connected (e.g., bonded) at a proximal end to guidewire cannula 616 and inflation cannula 628. Once balloon 620 is sealed at each end, balloon 620 is inflated. The delivery cannulas are aligned on inflated balloon 620 with a distal end at reference point corresponding to a distal end of proximal taper wall 622 of balloon 620. Distal ends of the delivery cannulas may be tapered to approximate or match a plane defined by medial working length 624 of balloon 620 when balloon 620 is in an inflated state. The delivery cannulas may then be glued or affixed to balloon 620 through an adhesive such as a cyanoacrylate adhesive. Next, sheath ring 625 is loaded (advanced proximal to distal) onto a proximal end of balloon 620 and the cannulas of catheter assembly 600 (e.g., guidewire cannula 616, inflation cannula 628, delivery cannula 630 and delivery cannula 632. A material of sheath ring 625 of a polymer such as PEBAX 40D™ may be connected to balloon 620 and the delivery cannulas by a thermal seal process. As an alternative to a thermal seal process for connecting sheath ring 625, sheath ring 625 may be connected to balloon 620 and the delivery cannulas by an adhesive, such as cyanoacrylate adhesive.

As noted above, each delivery cannula (e.g., delivery cannula 630, delivery cannula 632) folds up or bends distal to sheath ring 625 with the inflation of balloon 620. Thus, the path to be traveled by each needle (e.g., needle 634 and needle 636) crosses this bend or fold. To facilitate travel through a bend or folded region in each delivery cannula and to inhibit puncturing of the respective delivery cannula, each delivery cannula may include a deflector disposed along an interior wall. Representatively, a suitable deflector includes a ribbon of thin, generally flexible and generally resilient material (e.g., thickness on the order of about 0.0005 inches to about 0.003 inches and width on the order of about 0.005 inches and 0.015 inches). Suitable deflector materials, dimensions and connections within a catheter assembly are described in commonly-owned, U.S. patent application Ser. No. 09/746,498, filed Dec. 21, 2000 (now U.S. Pat. No. 6,692,466); U.S. patent application Ser. No. 10/394,834, filed Mar. 20, 2003; and U.S. patent application Ser. No. 10/749,354, filed Dec. 31, 2003.

Referring again to FIG. 6, proximal portion 613 of catheter assembly 600 is intended, in one embodiment, to reside outside a patient while the remainder of catheter assembly 600 is percutaneously introduced into, for example, the cardiovascular system of a patient via a brachial, a radial or a femoral artery. In this embodiment, proximal portion 613 of catheter assembly 600 includes hub 640. A similar hub was illustrated with reference to FIG. 5. Hub 640 includes needle 634 and needle 636, and inflation cannula 628. In one embodiment, relative to the materials for the various cannulas described, a housing of hub 640 is a hard or rigid polymer material, e.g., a polycarbonate or acrylonitrile butadiene styrene (ABS). A distal end of hub 640 has an opening to accommodate a proximal end of catheter body 612. Hub 640 also has a number of cavities at least partially therethrough (extending in a distal to proximal direction) to accommodate needle 634 and needle 636, and inflation cannula 628. A proximal portion of hub 640 flares to separate a spacing between the needles, and inflation cannula 628.

FIG. 6 shows a proximal end of needle 634 and needle 636 each connected (e.g., through an adhesive) to respective injection port 644 and injection port 646. In one embodiment, each injection port includes a luer fitting for conventional syringe attachment. A similar luer fitting may be used in the assembly described with reference to FIG. 5. Each injection port allows for the introduction of a composition, including but not limited to an active agent and a stimuli-responsive polymer. It is appreciated that a composition introduced at injection portion 644 and injection port 646 may be the same or different (e.g., a composition including a treatment agent and a stimuli-responsive polymer that will be released immediately versus a composition including a treatment agent and a stimuli-responsive polymer in which the treatment agent will be released over time (sustained release); a composition including a treatment agent and a stimuli-responsive polymer in which the treatment agent is an anti-inflammatory agent versus a composition including a treatment agent and a stimuli-responsive polymer in which the treatment agent is an anti-proliferative agent, etc.). In this embodiment, inflation cannula 628 terminates at the distal end of balloon inflation port 648.

In one embodiment, catheter assembly 600 (or catheter assembly 500 in FIG. 5) also includes or can be configured to include an imaging assembly. Suitable imaging assemblies include ultrasonic imaging assemblies, optical imaging assemblies, such as an optical coherence tomography (OCT) assembly, magnetic resonance imaging (MRI).

Figure 7:
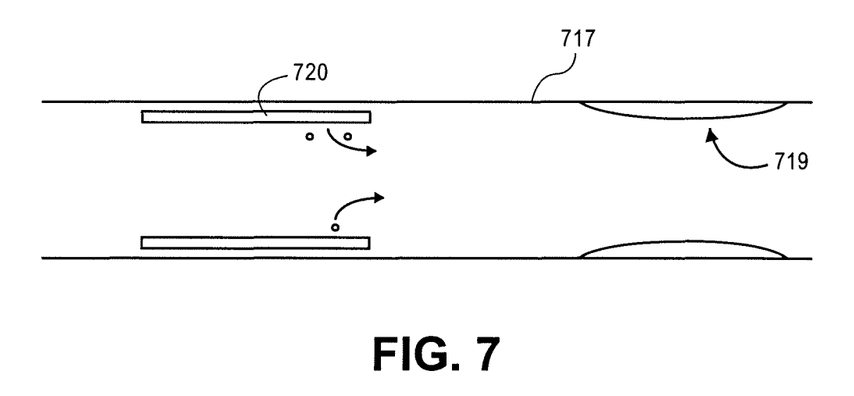
FIG. 7 shows a stent coated with an active agent/stimuli-responsive polymer disposed at a location in a blood vessel near a treatment site.

FIG. 7 shows an embodiment of a scaffold (e.g., a stent) placed in a region of a blood vessel including a lesion, such as atherosclerotic plaque. FIG. 7 shows blood vessel 717 including lesion 719 with stent 720 deployed proximal to (e.g., upstream of) the area of plaque 710. Stent 720 may have been deployed in the blood vessel percutaneously by, for example, a stent delivery catheter.

In one embodiment, stent 720 is composed of a metal, an alloy, a polymer, or a combination thereof and cholesterol-absorbing carrier molecules included in a stent coating or in the body of the stent. Examples of materials used to form stents include, but are not limited to, ELATINITE®, nitinol (nickel-titanium alloy), stainless steel, tantalum, tantalum-based alloys, platinum, platinum-based alloys, and other metals and their alloys. Alternatively, stent 720 is composed of a bioabsorbable polymer or biostable polymer. A polymer or coating is "bioabsorable" or "biodegradable" when it is capable of being completely or substantially degraded or eroded when exposed to either an in vivo environment or an in vitro environment having physical, chemical, or biological characteristics substantially similar to those of the in vivo environment within a mammal. A polymer or coating is "degradable or erodable" when it can be gradually broken down, resorbed, absorbed and eliminated by, for example, hydrolysis, enzymolysis, metabolic processes, bulk or surface erosion, and the like within a mammal. It is to be appreciated that traces of residue of polymer may remain following biodegradation. A "biostable" polymer is a polymer that is not bioabsorbable.

Suitable polymers used in embodiments of a material for stent 720, include, but are not limited to, hydrophobic, hydrophilic, amphiphilic, biodegradable, or a combination thereof. Examples of hydrophobic polymers include, but are not limited to, poly (ester amide), polystyrene-polisobutylene-polystyrene block copolymer (SIS), polystyrene, polyisobutylene, polycaprolactone, poly (L-lactide), poly (D,L-lactide), polylactic acid (PLA), poly (lactide-co-glycolide), poly (glycolide), polyalkylene, polyfluoroalkylene, polyhydroxyalkanoate, poly (3-hydroxybutyrate), poly (4-hydroxybutyrate), poly (3-hydroxyvalerate), poly (3-hydroxybutyrate-co-3-hydroxyvalerate), poly (3-hydroxyhexanoate), poly (4-hydroxyhexanoate), mid-chain polyhydroxyalkanoate, poly (trimethylene carbonate), poly (orthoester), polyphosphohazene, poly (phosphoester), poly (tyrosine derived arylates), poly (tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene (PVDF-HFP), poly (vinylidene fluoride-co-chlorotrifluoroethylene) (PVDF-CTFE), poly (butyl methacrylate), poly (methyl methacrylate), poly (vinyl acetate) (PVA), poly (ethylene-co-vinyl acetate), poly (ethylene-co-vinyl alcohol), poly (ester-urethane), poly (ether-urethane), poly (carbonate-urethane), poly (silicone-urethane), poly (2-hydroxyethyl methacrylate), SOLEF® polyvinylidene fluoride (PVDF), poly (urea-urethane), and combinations thereof.

Examples of hydrophilic polymers include, but are not limited to, polymers and co-polymers of hydroxyethly methacrylate (HEMA); poly (methyl methacrylate) (PMMA); poly (ethylene glycol) acrylate (PEGA); PEG methacrylate; phosphorylcholine; 2-methacryloyloxyethyl phosphorylcholine (MPC); n-vinyl pyrrolidone (VP); carboxylic acid bearing monomers such as methacrylic acid (MA), acrylic acid (AA); hydroxyl bearing monomers such as HEMA, hydroxypropyl methacrylate (HPMA), hydroxypropylmethacrylamide, alkoxymethacrylate, alkoxyacrylate, and 3-trimethylsilylpropyl methacrylate (TMSPMA), poly (ethylene glycol) (PEG), poly (propylene glycol) (PPG), SIS-PEG-polystyrene-PEG, polisobutylene-PEG, PCL-PEG, PLA-PEG, PMMA-PEG, PDMS-PEG, PVD-PEG, PLURONIC® surfactants (poly-propylene oxide-co-polyethylene glycol), poly (tetramethylene glycol), hydroxyfunctinal poly (vinyl pyrrolidone), polyalkylene oxide, dextran, dextrin, sodium hyaluronate, hyaluronic acid, heparin, elastin, chitosan; and combinations thereof.

Examples of biodegradable polymers include, but are not limited to, polymers having repeating units such as, for example, an α-hydroxycarboxylic acid, a cyclic diester of an α-hydroxycarboxylic, a dioxanone, a lactone, a cyclic carbonate, a cyclic oxalate, an epoxide, a glycol, an anhydride, a lactic acid, a glycolic acid, a glycolic acid, a lactide, a glycolide, an ethylene oxide, an ethylene glycol, or combinations thereof.

In some embodiments, the biodegradable polymers include, but are not limited to, polyesters, polyhydroxyalkanoates (PHAs), poly (ester amides), amino acids, PEG and/or alcohol groups, polycaprolactones, poly (L-lactide), poly (D,L-lactide, poly (D,L-lactide-co-PEG) block copolymers, poly (D,L-lactide-co-trimethylene carbonate), polyglycolides, poly (lactide-co-glycolide), polydioxanones, polyorthoesters, polyanhydrides, poly (glycolic acid-co-trimethylene carbonate), polyphosphoesters, polyphosphoester urethans, poly (amino acids), polycyanoacrylates, poly(trimethylene carbonate), poly (imino carbonate), polycarbonates, polyurethanes, copoly (ether-esters) (e.g., PEO/PLA), polyalkylene oxalates, polyphosphazenes, PHA-PEG, and any derivatives, analogs, homologues, salts, copolymers and combinations thereof.

A composition including a treatment agent (or multiple treatment agents) and a stimuli-responsive polymer may be included in a stent coating on stent 720 or included in the body of stent 720 such as, for example, a biodegradable polymeric stent. The release profile of the particles of treatment agent and polymer can be controlled by tailoring the chemical composition and crystallinity of the polymer as the coating or the bioabsorbable stent material (e.g., the more crystalline the slower the release rate).

Figure 8:
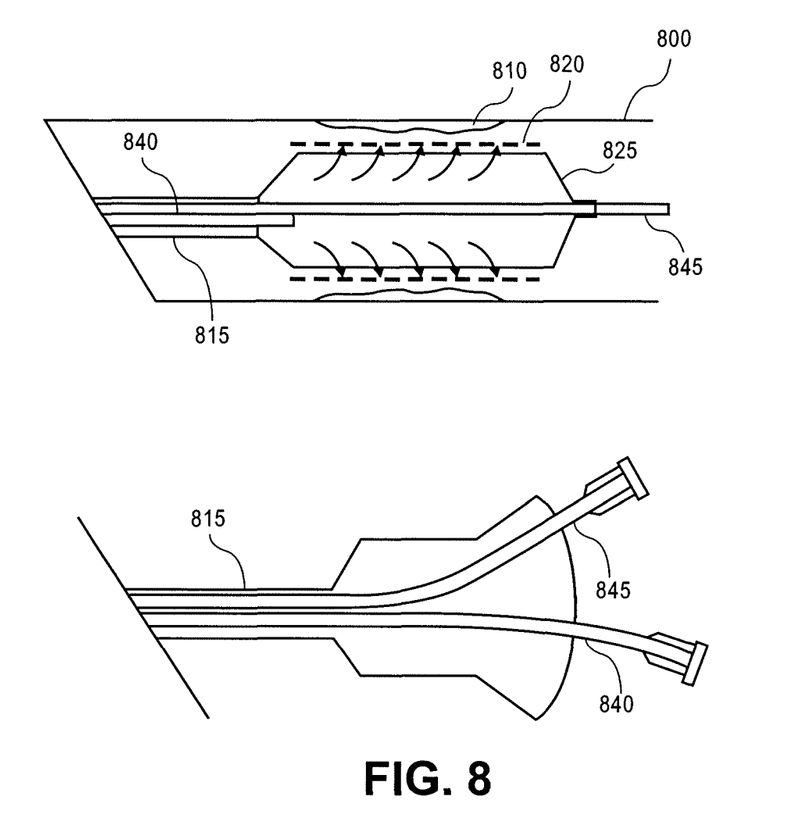
FIG. 8 shows a schematic cross-sectional side view of a catheter assembly in a blood vessel including a porous balloon.

In another embodiment, a composition including treatment agent (or multiple treatment agents) and a stimuli-responsive polymer may be delivered locally in combination with stent delivery (e.g., at the time of stent delivery or at a time thereafter). FIG. 8 shows a catheter assembly within a blood vessel. In this embodiment, blood vessel 800 includes lesion 810 such as atherosclerotic plaque or vulnerable plaque. A catheter assembly including balloon 825 is positioned in blood vessel 800 with the balloon at a position adjacent plaque 810. In this embodiment, balloon 825 is shown partially expanded and shown carrying, or acting as a carrier of stent 820. In one embodiment, balloon 825 may be inflated sufficient to place stent 820 against the wall of blood vessel 800, possibly at a position enveloping plaque 810 or at a position proximal to plaque 810. A proximal end or skirt of balloon 825 is connected to a distal end of primary cannula or tube 815 that is, for example, percutaneously, transluminally inserted through, for example, a femoral or radial artery. Primary cannula 815 has a lumen therethrough that includes guidewire cannula 845 (extending in an over-the-wire (OTW) fashion through balloon 825) and inflation cannula 840.

In the embodiment shown in FIG. 8, balloon 825 may be porous so that a treatment agent or a treatment agent or agents in a stimuli-responsive polymers (e.g., nanoparticles or microparticles) may be delivered through pores in the working length of porous balloon 825. Representatively, balloon 825 may be a perfusion balloon of an elastomeric material such as nylon, PEBAX, polyurethanes, or PET with microholes to deliver the bioactive agent. Representatively, microholes may have a diameter on the order of one micron 100 microns. Alternatively, porous balloons constructed from extended polytetrafluoroethylene (ePTFE) such as an EASY STREET® balloon and ultra high molecular weight polyethylene (UHMWPE) with node and fibril structure can be used as a suitable material for balloon 825. Balloon 825 may be thermally bonded to primary cannula 815. Inflation cannula 840 extends from a proximal point exterior to a patient receiving the catheter and a distal end within balloon 825. In this embodiment, a solution containing the treatment agent(s) and polymer particles is delivered through inflation cannula 840 to inflate balloon 825 and deliver the particles into blood vessel 800. In one embodiment, balloon 825 is made of a porous material such as ePTFE. A suitable pore size for an ePTFE balloon material is on the order of one micron to 60 microns. The porosity of ePTFE material can be controlled to accommodate a treatment agent, flow rate or particle size by changing a microstructure of an ePTFE tape used to form a balloon, for example, by wrapping around a mandrel. Alternatively, pore size can be controlled by controlling the compaction process of the balloon or by creating pores (e.g., micropores) using a laser.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A compositions comprising a solution suitable for introduction into a blood vessel comprising particles comprising a treatment agent and a stimuli-responsive polymer having the following formula:

2. The composition of claim 1, wherein the treatment agent comprises one of an anti-inflammatory agent and an anti-proliferative agent.

3. The composition of claim 1, wherein the treatment agent is chemically attached to the polymer.

* * * * *